United States Patent [19]

Anderson et al.

[11] Patent Number: 5,221,628

[45] Date of Patent: Jun. 22, 1993

[54] BINDING OF AGGREGATED IMMUNOGLOBULIN OR IMMUNE COMPLEXES BY SERUM AMYLOID P COMPONENT

[75] Inventors: Byron E. Anderson, Morton Grove; Marilyn R. Brown, Evanston, both of Ill.

[73] Assignee: Northwestern Univeristy, Evanston, Ill.

[21] Appl. No.: 672,526

[22] Filed: Mar. 19, 1991

[51] Int. Cl.$^5$ ............... G01N 33/564; G01N 33/543
[52] U.S. Cl. .................................. 436/507; 436/501; 436/509; 436/518; 436/536; 436/538; 436/808; 435/7.1; 435/7.8; 435/975
[58] Field of Search ............... 435/7.1, 7.8, 971, 975; 436/506, 507, 536, 538

[56] References Cited

FOREIGN PATENT DOCUMENTS 8909628 10/1984 World Int. Prop. O. .

OTHER PUBLICATIONS

Breathnach, Stephen M. "Tissue Amyloid P Components in Normal Human Dermis is Non-Covalently Associated with Elastic Fiber Microfibrils" J. Invest. Derm. 92:53–58 (1989).
Bristow, Cindy L. et al. "Evidence for the Binding of the Human Serum Amyloid P Component to C1q and Fab$_\gamma$," Mol. Immunol. 23:1045–1052 (1986).
Boxer, G. J., et al., Blood, 50:260 (Abstr.) (1977).
Chudwin, D. S., et al., J. Allergy Clin. Immunol., 77:216a (1986).
Clayton, J., et al., Cell Pathol., 43:63–66 (1983).
Gupta, R. C., et al., Arthritis and Rheumatism, 31:R39a (1988).
Hamazaki, H., B.B.R.C., 150:212–218 (1988).
Ingram, D. G., Animal Models of Immunological Processes, pp. 221–253 (1982).
Levinson, et al., J. Clin. Immunol., 7:328–336 (1984).
Liberti, P. A., et al., J. Immunol., 123:2212–2219 (1979).
Nilsson, I. M., et al., In Factor VIII Inhibitors, pp. 225–241 (1984).
Ohnishi, S., J. Biochem., 100:849–858 (1986).
Painter, R. H., et al., Ann. N.Y. Acad. Sci., 389:199–214 (1982).
Pepys, M. B., et al., B.B.R.C., 148:308–313 (1987).
Potempa, L. A., et al. Protides of the Biological Fluids, 34:287–290 (1986).
Schur, P. H., N. Engl. J. Med., 298:161–162 (1978).
Theofilopoulos, A. N., et al., Hospital Practice, pp. 107–121 (1980).
Theofilopoulos, A. N., et al., Adv. Immunol., 28:89–221 (1979).
Theofilopoulos, A. N., et al., Immunodiagnostics of Cancer, pp. 896–937 (M. Decker Inc., New York 1979).
Baltz, M. L., Biochim. Biophys. Acta, 701:229–236 (1982).
Baltz, M. L., et al., Clin. Exp. Immunol., 66:691–700 (1986).
Bertram, et al., J. Biol. Resp. Mod., 3:235–240 (1984).
Breathnach, S. M., J. Invest. Derm., 92:53–58 (1989).
Bristow, C. L., et al., Mol. Immunol., 23:1045–1052 (1986).
Bruneau, et al., J. Clin. Invest., 64:191 (1979).
Chu, E. B., et al., Amer. Assoc. Cancer Res., 29:371a (1988).
Creighton, et al., J. Immunol., 111:1219 (1973).

Primary Examiner—Christine M. Nucker
Assistant Examiner—Chris Dubrule
Attorney, Agent, or Firm—Willian Brinks Olds Hofer Gilson & Lione

[57] ABSTRACT

A method of binding aggregated immunoglobulin or immune complexes comprising contacting them with serum amyloid P component ("SAP"). The invention also comprises methods of using SAP to detect or quantitate immune complexes and to deplete fluids of aggregated immunoglobulin or immune complexes for diagnostic or therapeutic purposes. Also provided is a test kit comprising SAP for detecting or quantitating immune complexes and a device for removing aggregated immunoglobulin or immune complexes from fluids.

9 Claims, 3 Drawing Sheets

OTHER PUBLICATIONS

DeBeer, F. C., et al., *J. Exp. Med.*, 154:1134–1149 (1981).
Dobre, et al., J. Immunol. meth., 66:171–178 (1984).
Dougherty, T. J., et al., *Protides of the Biological Fluids*, 34:291–293 (1986).
Dyck, R. F., et al., *J. Exp. Med.*, 152:1162–1174 (1980).
Emancipator, et al., *Lab. Invest.*, 54:475–478 (1986).
Fiedel, B. A., et al., *J. Immunol.*, 131:1416–1419 (1983).
Floyd-Smith, G., et al., *Immunogenetics*, 24:171–176 (1986).
Guedson, J., et al., *J. Histochem. & Cytochem.*, 27:1131–1139 (1979).
Habeeb, A., *Analyt. Biochem.*, 14:328–336 (1966).
Hamazaki, H., *J. Biol. Chem.*, 262:1456–1460 (1987).
Hamazaki, H., *J. Biol. Chem.*, 261:5455–5459 (1986).
Hay, et al., *Clin. Exp. Immunol.*, 24:396–400 (1976).
Herriot, R., et al., *J. Pathol.*, 157:11–14 (1989).
Hind, C. R., et al., *J. Exp. Med.*, 159:1058–1069 (1984).
Hutchcraft, C., *Ann. N.Y. Acad. Sci.*, 389:449–450 (1982).
Jones, et al., *J. Immunol. Methods*, 53:201–208 (1982).
Khan, A. M., et al., *Placenta*, 6:551–554 (1985).
Kubak, B. M., et al., *Mol. Immunol.*, 25:851–858 (1988).
Kushner, I., *Ann. N.Y. Acad. Sci.*, 389:39–45 (1982).
Lai, K. N., et al., *Artificial Organs*, 11:259–264 (1987).
Li, J. J., et al., *Scand. J. Immunol.*, 19:227–236 (1984).
Mantzouranis, E. C., et al., *J. Biol. Chem.*, 260:7752–7756 (1985).
Melvin, T., *Am. J. Pathol.*, 125:460–464 (1986).
Mortensen, R. F., et al., *J. Immunol.*, 119:1611 (1977).
Nauts, *Host Defense Against Cancer and Its Potentiation*, pp. 337–351 (1975).
Nilsson, et al., *Scand. J. Haematol.*, 30:458–464 (1983).
Nilsson, I. M., et al., *Plasma. Ther. Transfers. Technol.*, 5:127–134 (1984).
Osmand, A. P., et al., *Proc. Nat. Acad. Sci.*, 74:739–743 (1977).
Pepys, M. B., et al., *Nature*, 278:199–201 (1979).
Pepys, M. B., et al., *Clin. Exp. Immunol.*, 38:284–293 (1979).
Pereira, et al., *J. Immunol.*, 125:763–770 (1980).
Perkins, S. J., et al., *Protides of the Biological Fluids*, 34:323–326 (1986).
Potempa, L. A., et al., *Mol. Immunol.*, 20:1165–1175 (1983).
Potempa, L. A., et al., *Inflammation*, 12:391–405 (1988).
Potempa, L. A., et al., *J. Biol. Chem.*, 260:12142–12147 (1985).
Prelli, F., et al., *J. Bio. Chem.*, 260:12895–12898 (1985).
Randerson, D. H., et al., *Artificial Organs*, 6:43–49 (1982).
Rostagno, A., et al., *B.B.R.C.*, 140:12–20 (1986).
Sarlo, K. T., et al., *Cell. Immun.*, 106:273–286 (1987).
Sarlo, K. T., *Cell. Immunol.*, 93:398–405 (1985).
Serban, D., et al., *Scan. J. Immunol.*, 25:275–281 (1987).
Singh, et al., *J. Immunol. Meth.*, 50:109–114 (1982).
Terman, et al., *New Engl. J. Med.*, 305:1195–2000 (1981).
Theofilopoulos, et al., *J. Clin. Invest.*, 61:1570 (1978).
Tseng, J., et al., *Immunol. Invest.*, 15:749–761 (1986).
Woo, P., et al., *J. Biol. Chem.*, 260:13384–13388 (1985).

BINDING OF AGGREGATED IMMUNOGLOBULIN OR IMMUNE COMPLEXES BY SERUM AMYLOID P COMPONENT

FIELD OF INVENTION

This invention relates to a method of binding aggregated immunoglobulin or immune complexes using serum amyloid P component ("SAP"), a naturally-occurring protein. In particular, this invention relates to the use of SAP in in vitro assays for detecting and quantitating immune complexes. The invention further relates to the use of SAP for therapeutic purposes in the treatment of diseases. The invention also relates to test kits comprising SAP for detecting and quantitating immune complexes and to devices for removing immune complexes from fluids.

BACKGROUND OF THE INVENTION

Immune complexes are formed by the binding of antibodies, consisting of various types of immunoglobulins, with antigens. The production of antibodies and formation of immune complexes is part of the immune response of an individual to combat disease.

Many diseases of autoimmune, infectious, or malignant nature are characterized in part by the presence of immune complexes in the blood. These complexes may remain in the circulation for long periods of time and deposit in various tissues, such as the lung, kidney, and heart, contributing to the inflammatory and erosive manifestations of autoimmune and other diseases. [See Emancipator, et al., *Lab. Invest.*, 54:475-478 (1986)]. Prolonged presence of immune complexes in the circulation and in tissues contributes to a compromised immune system function and inflammatory pathology.

Immune complexes may be cleared from the circulation and from tissues by a variety of mechanisms. One naturally-occurring mechanism is the acute phase response. An acute phase response is the group of metabolic and systemic physiological changes an organism undergoes following a trauma, such as an infection, injury, or disease. At the tissue level, this response manifests itself as inflammation. At the organismal level, this response is characterized by changes in cellular populations and their functions. For example, circulating macrophages and fixed macrophages found in the liver, spleen, and lymph nodes, may remove immune complexes.

The acute phase response is also characterized by changes in concentrations of various metals and proteins in the circulation. Serum amyloid P component ("SAP") and C-reactive protein ("CRP") are examples of two serum proteins, the concentrations of which can increase rapidly and dramatically during an acute phase response. In humans undergoing acute phase responses, serum concentrations of SAP may fluctuate but do not rise significantly. In contrast, CRP serum concentrations can increase 1000-fold in humans during an acute phase response. In other species, however, SAP serum concentrations do increase. For example, murine SAP concentrations increase up to 50-fold during an induced acute phase response. Accordingly, SAP is considered an acute phase reactant ("APR") in mice but not in humans. [See Kushner, I., *Ann. N.Y. Acad. Sci.*, 389:39-45 (1982); Pepys, M. B., et al., *Nature*, 278:199-201 (1979)].

Another mechanism by which immune complexes may be removed from the circulation is through plasma exchange or blood filtration therapy. Generally, for blood filtration therapy, a substance which can bind aggregated or complexed immunoglobulin is immobilized on a solid support which is encased in an extracorporeal device, through which whole blood or plasma is passed. In some cases, after passage over the adsorbent, blood components are reinfused into the individual thus eliminating the need for large amounts of replacement plasma or other replacement fluids. Published studies indicate that the removal of circulating immune complexes, or enhancing their clearance from the circulation, may constitute an effective therapeutic treatment. [See Theofilopoulos, A. M., et al., *Adv. Immunol.*, 28:90-220 (1979); Theofilopolous, A. M., et al., *Immunodiaonostics of Cancer*, p. 896 (M. Decker Inc., New York 1979)].

Many investigators have devised assays and adsorbents to selectively react with immune complexes as a means of monitoring and removing immune complexes from fluids. Various methods have been used to assay for immune complexes, including the following: physical separation using polyethylene glycol; reducing the temperature of the solution containing the immune complexes (i.e., cold precipitation); binding of the immune complexes to complement protein C1q or to antibodies specific to the complement protein C3 and C3 degradation products; binding of the immune complexes to rheumatoid factors; binding to the bovine protein conglutinin; or binding of the immune complexes to platelets or to the Raji lymphoblastoid cell line. [See Theofilopoulos, A. M., et al., *Hosp. Pract.*, pp. 107-121 (February 1980); Ingram, *Animal Models of Immunological Processes*, pp. 221-253 (1982); Levinsson, et al., *J. Clin. Immunol.*, 7:328-336 (1984); Singh, et al., *J. Immunol. Meth.*, 50:109-114 (1982); Hay, et al., *Clin. Exp. Immunol.*, 24:396-400 (1976); Pereira, et al., *J. Immunol.*, 125:763-770 (1980); Theofilopoulos, et al., *J. Clin. Invest.*, 61:1570 (1978); Creighton, et al., *J. Immunol.*, 111:1219 (1973); Schur, *N. Engl. J. Med.*, 298:161 (1978); Bruneau, et al., *J. Clin. Invest.*, 64:191 (1979)].

There are advantages to each of the aforementioned methods, as well as disadvantages which include insensitivity, nonspecificity, inability to detect immune complexes of all sizes and of all immunoglobulin isotypes and subisotypes, reliance on immune complexes containing complement proteins, and interference by non-complexed immunoglobulins. Therefore, results gathered by any of these methods and assays may be considered to be of marginal value for diagnostic purposes.

Other methods have been developed in which various adsorbents, immobilized on solid supports, are used for binding immune complexes. The use of Staphylococcal A (the various subtypes collectively known as "Protein A") as an immobilized immune complex adsorbent has had mixed results. The failure of Protein A as an adsorbent is presumably due to its inability to effectively differentiate the aggregated immunoglobulin of immune complexes from "noncomplexed" immunoglobulin. [See Betram, et al., *J. Biol. Resp. Mod.*, 2:235-240 (1984); Terman, et al., *New Engl. J. Med.*, 305:1195-2000 (1981); Dobre, et al., *J. Immunol. Meth.*, 66:171-178 (1984); Nilsson, et al., *Scand. J. Haematol.*, 30:458-464 (1983); Nauts, *Host Defense Against Cancer and Its Potentiation*, pp. 337-351 (1975)]. Because protein A binds to the "Fc" portion of immunoglobulins, investigators have also proposed or attempted using other Fc receptors, such as C1q or rheumatoid factor, or a specific antigen or antibody, as immobilized immunoadsorbents. [See Nilsson, I. M., et al., *Plasma. Ther. Transfers. Technol.*, 5:127-134 (1984); Lai, K. N., et al., *Artificial Organs*, 11:259-264 (1987), Nilsson, I. M., et al., *In Factor VIII Inhibitors*, p. 225 (1984); Liberti, P. A., et al., *J. Immunol.*, 123:2212-2219 (1979); Randerson, D. H., et al., *Artificial Organs*, 6:43-49 (1982)].

As described above, CRP is a protein whose serum concentration is known to significantly increase in humans during an acute phase response, and the CRP molecule has been monitored as a marker of acute inflammation. [See Potempa, L. A., et al., *Mol. Immunol.*, 20:1165-1175 (1983)]. CRP can also recognize and bind one of several ligands on the cell or bacterial surface, or in suspension. These ligands include phosphorylcholine, chromatin, and polycations. It appears that certain CRP-ligand complexes have the capacity to activate the complement pathway, thus stimulating certain aspects of the immune system.

The native form of CRP can be altered so as to have significantly different charge, size, solubility, and antigenicity characteristics. The distinctive antigenicity associated with altered CRP has been referred to as "neo-CRP," and the altered CRP molecule itself has been referred to as "modified-CRP." It has been determined that modified-CRP expressing neo-CRP antigenicity functions in a variety of in vitro assays which are useful in assessing the state of immune system reactivity. [See Potempa, L. A., et al., *Protides of the Biological Fluids*, 34:287-290 (1986); Potempa, L. A., et al., *Inflammation*, 12:391-405 (1988); Gupta, R. C., et al., *Arthritis & Rheumatism*, 31:R39a (1988); Chu, E. B., et al., *Amer. Assoc. Cancer Res.* 29:371a (1988); Doughery, T. J., et al., *Protides of the Biological Fluids*, 34:291-293 (1986)].

Modified-CRP has also been used in vivo. Mice injected with modified-CRP 30 minutes prior to receiving a lethal dose (90%) of type 7F *Streptococcus pneumoniae* survived death in a significant and dose-related manner. [See Chudwin, D. S., et al., *J. Allergy Clin. Immunol.*, 77:2169 (1986)].

Finally, as disclosed in PCT application WO 89/09628, modified-CRP, either in solution or immobilized on a solid surface, selectively binds aggregated immunoglobulin and immune complexes. This patent application describes the use of modified-CRP to detect and quantitate immune complexes and to remove aggregated immunoglobulin and immune complexes from fluids such as plasma. Also described is a method of reducing the levels of immune complexes in a mammal comprising administering modified-CRP to the mammal.

Serum amyloid P component ("SAP") is a naturally-occurring serum protein in mammals. SAP is a 250,000 molecular weight glycoprotein and is a member of the pentraxin family of structurally related proteins. [See Osmand, A. P., et al., *Proc. Nat. Acad. Sci.*, 74:739-743 (1977)]. It has been hypothesized that the genes encoding SAP and CRP arose from a gene duplication since the genes for both SAP and CRP have been mapped to the same human chromosome, and have been found to be partially, but significantly, structurally homologous. SAP has approximately 50% strict amino acid sequence homology with CRP. [See Floyd-Smith, G., et al., *Immunogenetics*, 24:171-176 (1986); Mantzousanis, E. C., et al., *J. Biol. Chem.*, 260:7752-7756 (1985); Ohnishi, S., *J. Biol. Chem.*, 100:849-858 (1986); Prelli, F., et al., *J. Bio. Chem.*, 260:12895-12898 (1985)].

The SAP molecule itself is quite different from CRP structurally. SAP circulates as two non-covalently associated pentamers, each of which consists of five identical non-covalently linked subunits. [See Painter, R. H., *Ann. N.Y. Acad. Sci.*, 389:199-215 (1982); Perkins, S. J., et al., *Protides of the Biological Fluids*, 34:323-326 (1986)]. While SAP exists as a decameric molecule in solution, CRP behaves as a pentamer in coexistence with higher oligomers. Id.

SAP aggregates and precipitates in high concentrations of ionic calcium. It has been suggested that SAP may aggregate and precipitate to form amyloid P component ("AP") in localized areas of increased ionic calcium concentration. [See Baltz, M. L., *Biochim. Biophys. Acta*, 701:229-236 (1982)]. AP is a normal constituent of glomerular basement membrane, human dermis, and cervix, testis, and placentae tissues. [See Baltz, M. L., et al., *Clin. Exp. Immunol.*, 66:691-700 (1986); Dyck, R. F., et al., *J. Exp. Med.*, 152:1162-1174 (1980); Melvin, T., *Am. J. Pathol.*, 125:460-464 (1986); Breathnach, S. M., *J. Invest. Derm.*, 92:53-58 (1989); Clayton, J., *Cell. Pathol.*, 43:63-66 (1983); Herriut, R., et al., *J. Pathol.*, 157:11-14 (1989); Khan, A. M., et al., *Placenta*, 6:551-554 (1985)].

SAP has binding interactions with both cells and ligands. Specifically, with respect to cellular binding, SAP has been shown to bind to elicited, but not quiescent, tissue macrophages, thereby exerting a strong, positive feedback affect on interleukin-1 elaboration. [See Sarlo, K. T., *Cell. Immunol.*, 93:398-405 (1985)]. Furthermore, SAP has been reported to inhibit CRP-induced platelet aggregation and to inhibit murine secondary antibody responses to T-cell dependent antigens in vitro. [See Fiedel, B. A., et al., *J. Immunol.*, 131:1416-1419 (1983); Sarlo, K. T., et al., *Cell. Immun.*, 106:273-286 (1987)].

The binding of SAP to ligands has also been demonstrated. Ligands of SAP include unsubstituted agarose, heparin, isolated amyloid fibrils, zymosan, fibronectin, C3bi, C4bp, C1q, and the Fab fragment of IgG. [See Painter, R. H., et al., *Ann. N.Y. Acad. Sci.*, 389:199-215 (1982); Boxer, G. J., et al., *Blood*, 50:260 (Abstr.) (1977); Pepys, M. B., et al., *Clin. Exp. Immunol.*, 38:284-293 (1979); Deeber, F. C., et al., *J. Exp. Med.*, 154:1134-1149 (1981); Tseng, J., et al., *Immunol. Invest.*, 15:749-761 (1986); Rostagno, A., et al., *B.B.R.C.*, 140:12-20 (1986); Hutchcraft, C., *Ann. N.Y. Acad. Sci.*, 389:449-450 (1982); Bristow, C. L., et al., *Mol. Immunol.*, 23:1045-1052 (1986)]. This binding has consistently shown to be calcium-dependent.

Also shown to be specifically bound by SAP in vitro have been various, but not all, glycosaminoglycans, immobilized native and denatured DNA, native chromatin, and H1-deficient chromatin. [See Hamazaki, H., *J. Biol. Chem.*, 262:1456-1460 (1987); Pepys, M. B., et al., *B.B.R.C.*, 148:308-313 (1987)].

The nature of the specific binding interactions between SAP and some of its cellular, tissue-bound, and soluble ligands has been investigated. The results of an investigation into the structure of pyruvate-rich agarose components to which SAP specifically and avidly binds suggest that a glycan structurally similar to calcium sequestering $\beta$-turns connecting antiparallel $\beta$-pleated sheaths in proteins were the target of SAP interactions. It has been proposed that $\beta$-pleated sheath secondary structure binds to SAP and becomes the associated AP component always found in these tissues. [See Hind, C. R., et al., *J. Exp. Med.*, 159:1058-1069 (1984)]. Galactans, but not galactose, competed with nonT, nonB ALL cells and peripheral blood mononuclear cells for labeled AP. Moreover, AP could be precipitated by two snail galactans in a dose-dependent manner. This suggests that appropriate conformation of a carbohydrate moiety is essential for SAP's binding and is supported by the finding that a human serum lectin (which was later identified as SAP) binds to the penultimate galactose residues in oligosaccharides but not well to terminal galactose residues, and not at all to fucose, N-acetylglucosamine, and mannose. [See Li, J. J., et al., *Scand. J. Immunol.*, 19:227-236 (1984); Hamazaki, H., *J. Biol. Chem.*, 261: 5455-5459 (1986); Hamazaki, H., *B.B.R.C.*, 150:212-218 (1988)]. However, SAP has been found to bind mannose-rich oligosaccharide sequences and mannose-terminated sequences. [See Kubak, B. M., et al., *Mol. Immunol.*, 25: 851-858 (1988)].

In a further effort to characterize SAP binding, SAP's binding to a panel of haptens was assessed. The results of these studies suggest that SAP has a single type of binding site which is capable of specifically binding a variety of ligands which share a single, as yet unidentified, characteristic. A model to explain this polyspecific binding by a single type of site is proposed in which SAP binds a calcium ion in such a way that it occupies only half of the ion's coordination sphere, the other half of which is then bound by SAP's ligand. In the absence of an exogenous ligand, it is proposed that the other half of the SAP-bound ionic calcium's coordination sphere is bound by other SAP binding sites within another, or the same, SAP molecule. This would explain the observed calcium-induced precipitation of SAP. Similar models can be invoked to explain the observation that copper can also induce SAP autoaggregation, as well as zymosan binding, under neutral and acidic conditions. [See Potempa, L. A., et al., *J. Biol. Chem.*, 260:12142-12147 (1985)].

The same panel of haptens has been used to study the calcium-dependent ligand binding characteristics of CRP. CRP was found to bind only two of the ligands tested, and the binding was poor. The very limited interaction of CRP with the panel of SAP ligands was interpreted as an indication that CRP-bound ionic calcium cannot form calcium bridges as can SAP-bound ionic calcium. [See Serban, D., et al., *Scan. J. Immunol.*, 25:275-281 (1987)].

The nature of the binding of fibronectin and elicited macrophages by SAP was analyzed by Scatchard analysis of competitive ELISA and radiolabeled-SAP binding assays. A Scatchard plot depicting the results of an ELISA in which the binding of soluble fibronectin to immobilized SAP was measured indicated that positive cooperativity was involved. The binding of radiolabeled-SAP to elicited macrophages exhibited all of the hallmarks of receptor binding (e.g., specificity, saturability, reversibility, and high affinity). There appeared to be approximately 200,000 of a single class of macrophage receptors with an equilibrium dissociation constant of $5 \times 10^{-8}$M per cell. Based upon competition studies and studies of the affect of deglycosylating SAP on its binding, it was proposed that the elicited macrophage receptor to which SAP binds is a cation-dependent mannose-6-phosphate receptor. This is in contrast to the macrophage receptor for CRP which has been found to be closely associated with the IgG Fc receptor. [See Mortensen, R. F., et al., *J. Immunol.*, 119:1611 (1977)].

SUMMARY OF THE INVENTION

The present invention comprises a method of binding aggregated immunoglobulin or immune complexes comprising contacting the aggregated immunoglobulin or immune complexes with SAP. SAP selectively binds aggregated immunoglobulin and immune complexes in the presence of monomeric immunoglobulin.

The ability of SAP to bind immune complexes can be utilized to detect or quantitate the immune complexes. To do so, the immune complexes are contacted with SAP immobilized on a solid surface so that they bind to the SAP, and then the immune complexes bound to the SAP are detected or quantitated.

The invention also comprises a method of removing aggregated immunoglobulin or immune complexes from fluids by contacting the fluid with SAP and separating the fluid from the aggregated immunoglobulin or immune complexes bound to the SAP. This aspect of the invention is particularly useful for removing immune complexes from the body fluid of a mammal in need thereof, and to remove aggregated immunoglobulin or immune complexes from fluids used in therapeutic (e.g., gamma globulin) or diagnostic (e.g., antibody solutions) procedures.

Thus, the ability of SAP to bind aggregated immunoglobulin and immune complexes may be utilized in in vitro assays, in the therapeutic treatment of disease, and to remove unwanted aggregated immunoglobulin or immune complexes from fluids used in diagnostic or therapeutic procedures.

The invention further comprises a device for removing aggregated immunoglobulin or immune complexes from fluids comprising SAP bound to a solid support surface and a means for encasing the solid support surface so that the fluid may be contacted with the surface.

The invention also comprises a test kit for detecting or quantitating immune complexes comprising a container holding SAP. The SAP may be labeled to allow for the detection or quantitation of the immune complexes.

DETAILED DESCRIPTION OF THE PRESENTLY PREFERRED EMBODIMENTS

SAP useful in the practice of the invention includes the native form of SAP which may be isolated and prepared in a variety of ways. For example, native SAP may be prepared by standard procedures known in the art such as that described in Potempa, L. A., et al., *J. Biol. Chem.*, 260:12142-12147 (1985).

Modifications of standard procedures for isolating native SAP can also be used. As described in Example 1, isolated native SAP may be further purified by affinity chromatography against Protein G coupled to silica. The Protein G treatment removes any remaining IgGs from the SAP effluent. This SAP preparation, designated SAP/G-2 herein, is the preferred form of SAP for use in the present invention. The method of preparing SAP/G-2 is described in further detail in Example 1. Other suitable and equivalent modifications and preparations of SAP are also contemplated and will be apparent to those skilled in the art.

Native SAP treated with denaturing agents suc as urea can also be used, but the use of SAP modified in this manner does not appear to be particularly advantageous. As the Examples herein show, urea-treated SAP, designated C-SAP, has decreased binding to aggregated gamma globulin as compared to SAP/G-2.

According to the present invention, SAP may be utilized to bind aggregated immunoglobulin or immune complexes. Preferably, the SAP is coated and bound to a solid support surface before being contacted with a fluid containing the aggregated immunoglobulin or immune complexes. Fragments derived from SAP may have the biological functionality or binding capacity of SAP. Thus, the invention also contemplates the use of any such fragments that bind aggregated immunoglobulin or immune complexes.

With respect to SAP coated and bound to a solid support surface, the fluid may be incubated statically on the immobilized SAP for use in diagnostic assays, or may be passed dynamically across the immobilized SAP in an extracorporeal device for therapeutic treatment, i.e., binding immune complexes.

In selecting a solid support surface, consideration should be given to whether SAP will leach off the solid support surface. If so, the leaching must be minimized. The solid support surface may be a granular filtration material in a column or in an extracorporeal device, a microtiter well, or another suitable surface. Examples of solid support surfaces that may be utilized with the SAP of the present invention include, but are not limited to, agarose-based resins, polyacrylamide, polymethylmethacrylate, polycarbonate, polysulfone, polyacrylonitrile, polyethylene, polypropylene, latex beads, dextran, glass, nylon, polyvinyl alcohol, gels, clay, and cellulose derivatives as well as other polymeric materials. Generally, any polymeric material may be utilized which does not result in significant leaching of the SAP from the solid support surface. The polymeric material may be hydrophilic, hydrophobic, or both. The polymeric materials may also be shaped as beads for use in a column.

Column and solid support materials are commercially available in the United States from Bio Rad Laboratories (Richmond, CA); Pierce Chemical Co. (Rockford, Ill.); Pall Biosupport (Glen Cove, N.Y.); Micro Membranes (Neward, N.J.); Pharmacia Fine Chemicals (Uppsala, Sweden); and others.

SAP can be bound to the solid surface in a variety of ways well-known in the art. Preferably, isolated SAP is bound to a suitable hydrophobic or hydrophilic surface by incubating the SAP on the solid surface for a sufficient time to allow secure attachment of the SAP to the surface. Selecting appropriate times, temperature, and other conditions of the incubation are well within the skill in the art. Preferably, the SAP is applied to the surface at a concentration of about 1-9 $\mu$g/ml, and incubated for at least 2 hours at room temperature.

Linking agents known in the art may also be utilized for secure attachment of SAP to a solid surface. The linking agent may be incorporated as part of, or derivatized onto, the solid surface before SAP is added.

To remove aggregated immunoglobulin or immune complexes from fluids such as whole blood, plasma, other mammalian body fluids, or other immunoglobulin-containing materials, the blood, plasma or other fluid may be passed through an extracorporeal device having a solid surface coated with SAP and a means for encasing the solid surface so that the fluid may contact the solid surface. The duration of the contact is not bound to critical limits although it should, of course, be sufficient to allow aggregated immunoglobulin or immune complexes to be adsorbed to and bound by the SAP on the solid surface.

In laboratory practice, the SAP of the present invention may be used to remove aggregated immunoglobulin or immune complexes from fluids such as reagent materials or solutions, e.g., solutions containing monoclonal antibodies, derivitized reagents, intravenous gamma globulin, or isolated blood components, used for research or in therapeutic procedures or diagnostic tests. The presence of aggregated immunoglobulin in such reagents may be expected because of processing steps used to make these fluids, such as heat treatment of antisera to inactivate complement.

For therapeutic uses, SAP can be coated and bound on a solid support surface which is encased online in an extracorporeal device through which blood or plasma can be circulated dynamically so that the immune complexes contained therein are bound and thereby removed from the plasma or blood of any mammal, including humans. By this process, fluids can be returned to the patient, negating the need for blood replacement therapy. The process is thus applicable with conventional plasmapheresis or hemodialysis techniques.

The solid support surface and encasing means of the device may be made of any biocompatible material. For instance, the solid surface may be a membraneous surface, agarose-based beads, or hollow fibers coated with SAP. The extracorporeal device may be a column packed with beads, a hollow fiber membrane encased in a cylinder, a microtiter plate containing wells, or any suitable surface, coated with SAP. The device may also include appropriate tubing for connecting it to a patient and a pump to aid the passage of the fluid through the device and back into the patient and to prevent air from entering the system. The device must be sterilized for therapeutic use, and sterilization may be accomplished in conventional ways such as purging with ethylene oxide or by irradiating the device.

The invention also comprises a method of detecting or quantitating immune complexes comprising contacting the immune complexes with SAP so that the immune complexes bind to the SAP. The SAP is immobilized on a solid support surface of the types, and in the ways, described above. After the immune complexes are bound by the SAP on the solid support surface, they can be washed thoroughly while remaining bound to the surface. Such washing assures the removal of unbound components which could reduce the accuracy of the immune complex determination. To detect or quantitate the immune complexes, labeled SAP can be used. The labels useful in the invention are those known in the art such as enzyme and fluorescent labels.

Alternatively, the immune complexes can be detected or quantified using conventional immunoassay techniques by adding a labeled component that binds to the immune complexes or to the SAP. Such conventional immunoassay techniques include agglutination, radioimmunoassay, enzyme immunoassays, and fluorescence assays. Enzyme-linked immunosorbent assays (EIA) are preferred since they provide a means for sensitive quantitation of levels of immune complexes. The labeled components which may be added to the immune complexes bound to the SAP to allow for the detection or quantitation of the immune complexes are conventional reagents used in immunoassays. Also, the labels used are those known in the art. For example, enzyme-labeled, radioisotope-labeled, or biotin-labeled antibodies to the immunoglobulin or the antigen in the immune complexes could be utilized in the immunoassay.

Since body fluids from mammals normally contain immune complexes, comparison of the levels of immune complexes in a test sample from a mammal will have to be made to the normal levels found in mammals to identify levels of immune complexes indicative of a disease state.

A test kit for detecting or quantitating immune complexes is also part of the present invention. The kit comprises a container holding a solution of SAP or SAP coated and bound to a solid support surface. The solid support surfaces are the types described above, and the SAP is attached as described above. Thus, the container could be a bottle holding a solution of SAP, a dipstick coated with SAP encased in a protective package, a bottle holding latex beads coated with SAP, or a microtiter plate, the wells of which are coated with SAP. The SAP may be labeled if it is to be used for detecting or quantitating the immune complexes. Alternatively, the kit may further comprise a container holding the abovedescribed labeled component that allows for the detection or quantitation of the immune complexes when an immunoassay technique is used. The kit may also include other materials useful in performing the assay such as buffers, standards, microtiter plates, etc.

EXAMPLES

The invention is further illustrated by the following examples.

EXAMPLE 1

EIAs were performed to compare the binding of several concentrations of heat-aggregated human gamma globulin (HAg) and monomeric human gamma globulin (mIg) to solid phase-adsorbed preparations of SAP. Three different SAP preparations, designated SAP, SAP/G-2, and c-SAP, were tested to also compare the binding of SAP and modified-SAP to the ligands.

SAP was isolated from normal human serum by a modification of the standard procedure previously described. [See Potempa, L. A., et al., *J. Biol. Chem.*, 260:12142–12147 (1985)]. In this modified procedure, serum is obtained by centrifuging recalcified, outdated normal human plasma. Protease inhibitors are added to the serum, and the serum is incubated batchwise for four hours with one half volume unsubstituted Bio Gel A 0.5 m (BioRad Laboratories). The suspension is poured into a column, which is washed with a 10 mM Tris (pH 7.3) equilibration buffer, containing 150 mM NaCl and 2 mM $CaCl_2$, until the spectrophotometric absorbance at 280 nanometers is <0.05. The SAP is then eluted from the washed resin with a 10 mM Tris buffer (pH 7.3), containing 150 mM NaCl and 10 mM $Na_2EDTA$. Next, the eluate is fractionated by gel filtration chromatography using Bio Gel A 1.5 m. The column is then washed with a 20 mM Tris (pH 7.3) equilibration buffer, containing 300 mM NaCl and 10 mM $Na_2EDTA$. SAP which has been purified to this point will be designated herein as "SAP." The effluent fractions containing SAP are then pooled and affinity chromatographed against Protein G coupled to silica (HiPac Protein G LTQ) in order to remove any remaining IgGs from the Bio Gel A 1.5m effluent. This final SAP preparation will be designated herein as "SAP/G-2."

The preparation of modified-SAP, designated c-SAP, was prepared by incubating SAP for 1.5 hours at 37° C. in 8M urea in the presence of 10 mM $Na_2EDTA$. The solution was then exhaustively dialyzed against a 10 mM Tris buffer, pH 8.2.

Figure 4:
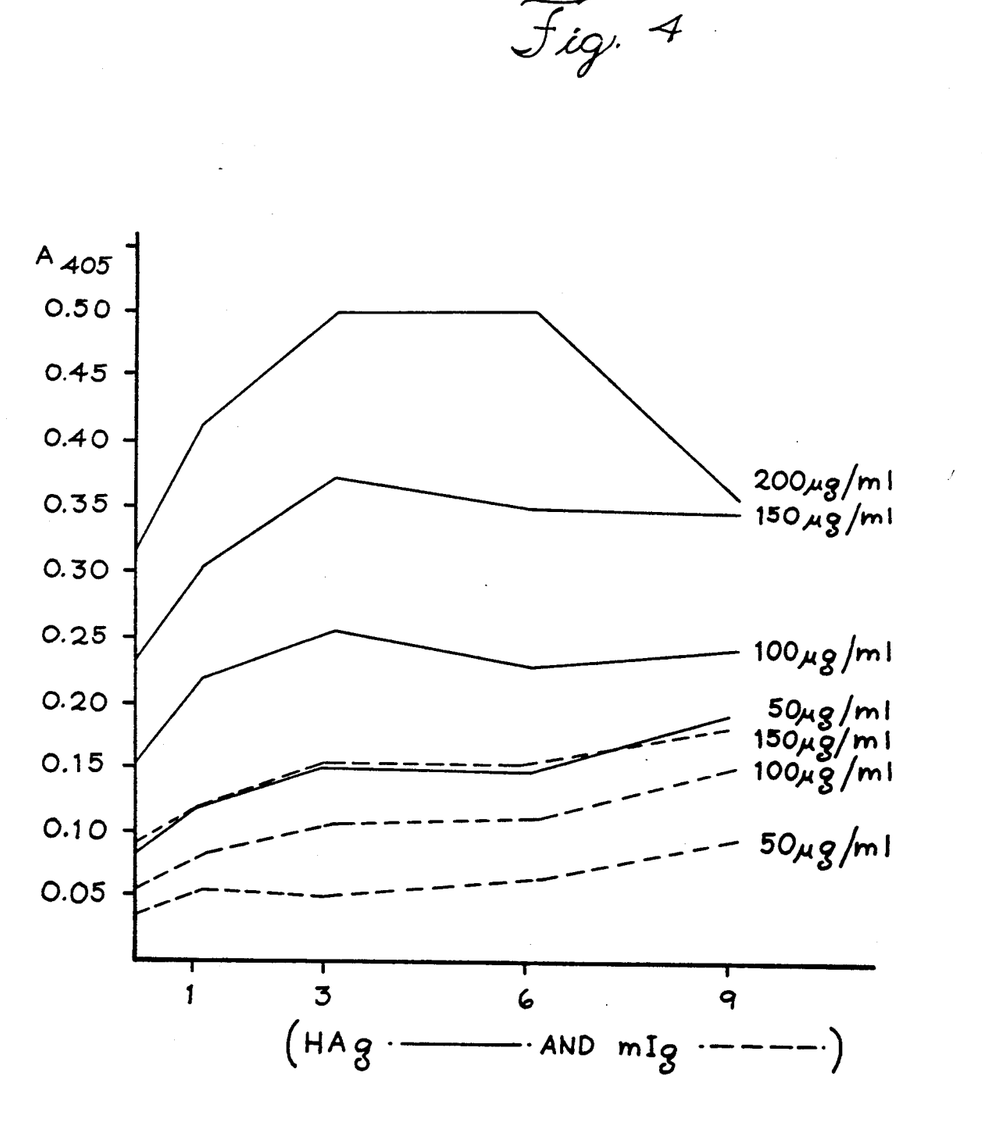
FIG. 4 shows dose-response binding of heat-aggregated human gamma globulin (HAg) and monomeric human gamma globulin (mIg) to SAP immobilized on polystyrene microtiter wells.

SAP, SAP/G-2, and c-SAP were then diluted to a final concentration of 3 $\mu g/ml$ in 0.1M $NaHCO_3$, pH 9. In an earlier dose-response experiment it had been determined that 3 $\mu g/ml$ was the optimal coating and binding concentration. This is shown in FIG. 4. In addition, a SAP/G-2 concentration of 6 $\mu g/ml$ was tested.

For the EIA, the basal surfaces of 96-well polystyrene microtiter plate (Nunc Immuno Plate Maxisorp F-96) wells were coated with 0.1 ml of either SAP, SAP/G-2, or c-SAP and incubated for 3 hours at 37° C. After incubation, the fluid in the well was aspirated off, and the well "blocked" by adding 0.2 ml of 1 mg/ml periodate-treated bovine serum albumin ("BSA"). The BSA was prepared by treating bovine serum albumin (bovine plasma fraction V - Sigma Chemical Co., St. Louis, Mo.) with sodium periodate to deglycosylate any molecules of BSA which may have been non-enzymatically glycosylated. A 7% solution of BSA was prepared by dissolving lyophilized BSA in phosphate buffered saline ("PBS") and an equal volume of 0.1M citrate, 0.2M $Na_2HPO_4$, 0.11M $NaIO_4$. This solution was incubated for 2 hours at 2°–8° C., then exhaustively dialyzed at 2°–8° C. against PBS.

The microtiter plates were incubated overnight at room temperature. The following morning, the wells were aspirated and washed three times with a PBS solution containing 1 mg/ml periodate-treated BSA and 0.1% Tween 20 ("BSAP").

The test ligands were prepared as follows. Heat-aggregated human gamma globulin ("HAg") (obtained from Immtech International, Inc.), was prepared by incubating human Cohn fraction II (Gammastan, Cutter Laboratories) for 30 minutes at 65° C. The preparation was fractionated by gel filtration through Bio Gel A 1.5 m (Bio Rad), and the effluent stored at 2°–8° C. Monomeric human gamma globulin ("mIg") (obtained from Immtech International, Inc.) was prepared the same as HAg except that the material was not heat-treated. Both HAg and mIg were diluted in Tris-buffered saline (10 mM Tris, 150 mM NaCl, 2 mM $CaCl_2$, pH 7.3) ("TBS-C").

Into each well, 0.1 ml of HAg or mIg (or TBS-C as a control) was added. The plate was incubated for 3.5 hours at 37° C., aspirated, and washed three times with BSAP.

To detect the amount of test ligand bound, 0.1 ml b-GtF(ab')$_2$ (biotinylated goat F(ab')$_2$ fragments against human IgG) (Cappel Laboratories) diluted 1:2000 in BSAP was added to each well. The wells were incubated for 2.5 hours at 37° C., aspirated, and washed three times with BSAP. Next, 0.1 ml of streptavidin-β-galactosidase (Bethesda Research Laboratories, Bethesda, Md.) diluted 1:2000 in BSAP was added to the wells and incubated for 2 hours at 37° C. Again, the wells were aspirated and washed three times with BSAP.

Finally, 0.1 ml of 4 mg/ml o-nitrophenyl galactopyranoside ("ONPG") (dissolved in 0.1M $Na_2HPO_4$, 5 mM $MgCl_2$, 0.1M β-mercaptoethanol, pH 7.3) was added to the wells and incubated for 30 minutes at room temperature. The color reaction was determined by light absorbance at 405 nanometers using a Titertek Multiscan Microtiter Plate Reader.

Figure 1:
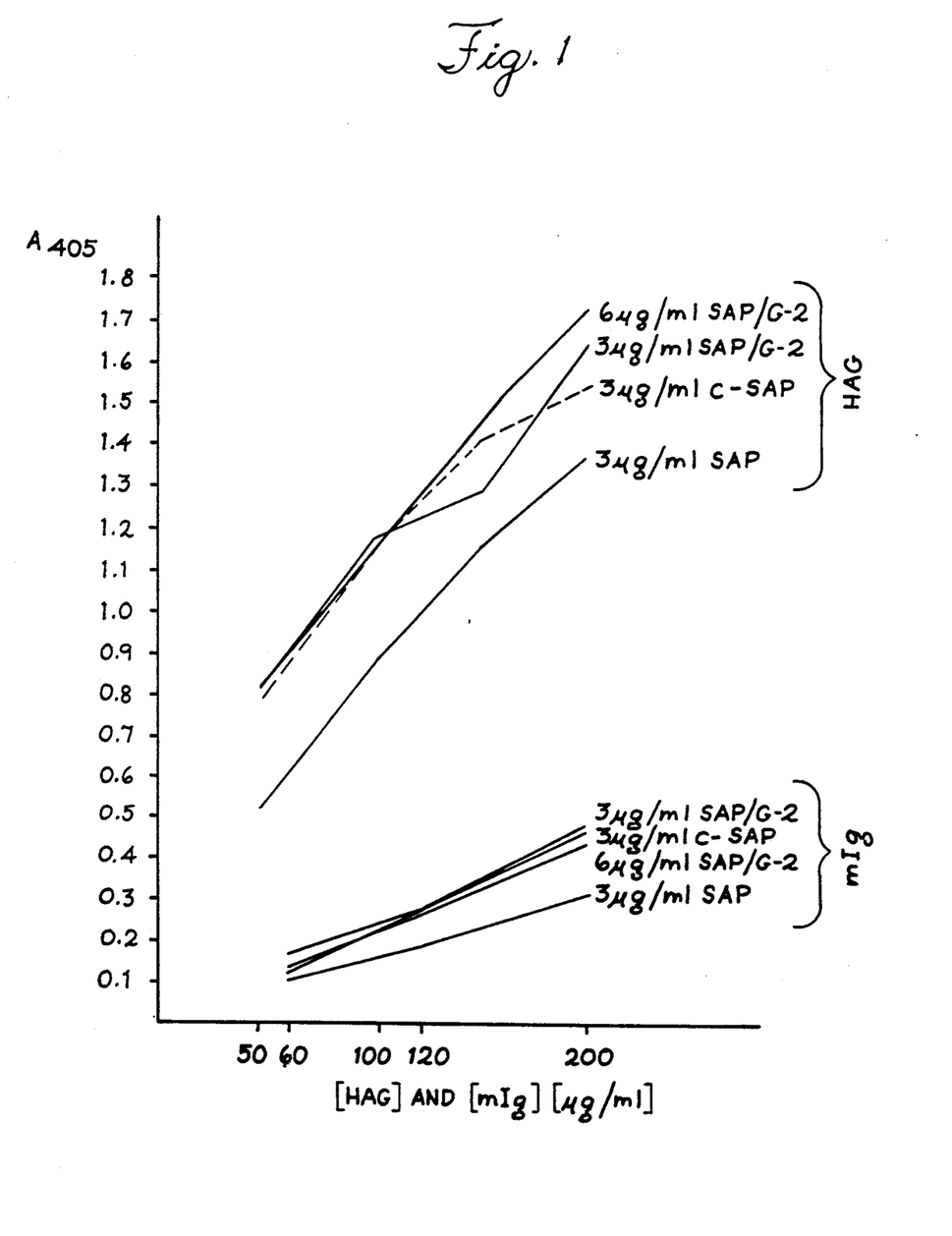
FIG. 1 shows the binding of heat-aggregated human gamma globulin (HAg) and monomeric human gamma globulin (mIg) to SAP and c-SAP immobilized on polystyrene microtiter wells.

The EIA results are shown in FIG. 1. The data shows that all three SAP preparations, SAP, SAP/G-2, and c-SAP, when adsorbed onto a solid surface, bind HAg preferentially as compared to mIg. At the SAP, SAP/G-2, and c-SAP concentrations tested, there is minimal binding to mIg and approximately a five-fold increase in binding to HAg as compared to mIg. The data also reveals that the modified form of SAP, c-SAP, does not exhibit enhanced binding to HAg as compared to SAP/G-2 binding.

EXAMPLE 2

EIAs were performed to determine the ability of solid phase-bound SAP to bind aggregated human gamma globulin ("AAG") in various concentrations of normal human serum ("NHS").

The reagents and EIA procedures are substantially the same as described in Example 1, except that the wells were first coated with 0.1 ml of 6 μg/ml SAP/G-2. After blocking and washing, 0.1 ml of either NHS, $AAg^b$, or TBS-C was added.

NHS was prepared by centrifuging whole blood (drawn without an anticoagulant). Human gamma globulin was alkali-aggregated by a standard method previously described. [See Jones, et al., J. Immunol. Methods, 53: 201-208 (1982)]. Lyophilized human gamma globulin (Sigma Chemicals) was solubilized in deionized water to a final concentration of 20 mg/ml. An equal volume of 0.2M NaOH was added to this solution, and incubated for 1 hour on ice with constant mixing. The resulting mixture (AAg) was exhaustively dialyzed against PBS and immediately frozen at −90° C. Aliquots were thawed and lightly biotinylated by the method described by Guedson, J., et al., J. Histochem. & Cytochem., 27:1131-1139 (1979). The AAg was diluted in an equal volume of 0.1M $NaHCO_3$, and NHS-LC-Biotin (Pierce Chemicals) was added and incubated for 1 our at room temperature. The resulting product, $AAg^b$, was then exhaustively dialyzed against PBS. The $AAg^b$ was determined by a TNBS assay to have approximately 14% of its lysine residues biotinylated. [See Habeeb, A., Analyt Biochem., 14:328-336 (1966)]. The NHS was serially diluted two-fold with TBS-C to a final volume of 0.5 ml. To each dilution, 0.01 ml of 5 mg/ml $AAg^b$ was added to prepare a solution of 100 μg/ml $AAg^b$ in concentrations of NHS ranging from 1:1 to 1:64.

After a two-hour incubation at 37° C. and several washes, streptavidin-β-galactosidase and ONPG were added as described in Example 1. The absorbance at 405 nm was then recorded.

Figure 2:
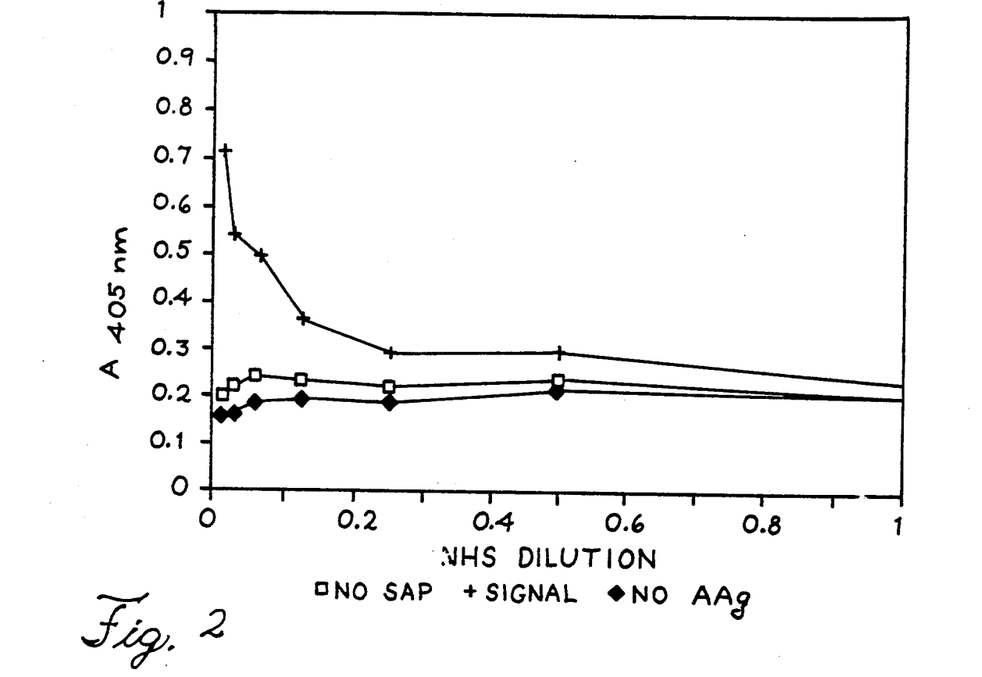
FIG. 2 shows the binding of alkali-aggregated human gamma globulin (AAg) in normal human serum (NHS) to SAP immobilized on polystyrene microtiter wells.

The results are shown in FIG. 2. At low dilutions (1:2 or 1:4 dilution) of NHS, SAP/G-2 bound little biotinylated AAg, indicating other serum components may be binding to the SAP/G-2 or may, in some other manner, be interfering with the binding to SAP/G-2. At 1:8, 1:16, 1:32, and 1:64 dilutions of NHS, biotinylated AAg bound to solid-phase adsorbed SAP/G-2.

EXAMPLE 3

EIAs were performed to determine the ability of solid-phase bound SAP to bind alkali-aggregated human gamma globulin (AAg) in normal human plasma (NHP). The EIA method and reagents used are substantially as described in Examples 1 and 2. First, 0.1 ml of 3 μg/ml SAP/G-2 was added to each of the wells. After blocking and washing, 0.1 ml of one of the following was added: AAg in NHP, NHP, TBS-C, or AAg in TBS-C.

NHP was prepared by centrifuging heparinized blood. The supernatant heparinized plasma was recovered and the cellular precipitate discarded. The NHP was then diluted two-fold with TBS-C. Alkali-aggregated human gamma globulin (AAg) (as prepared in Example 2) was added to each solution of NHP to a final concentration of 111 μg/ml.

Figure 3:
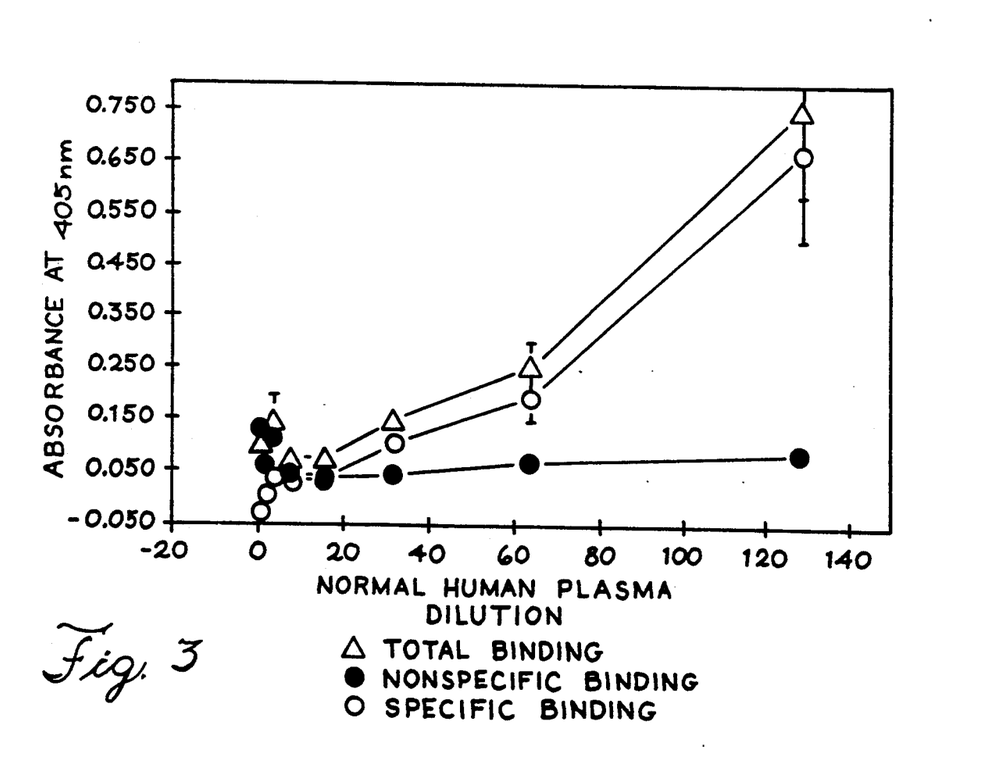
FIG. 3 shows the binding of alkali-aggregated human gamma globulin (AAg) in normal human plasma (NHP) to SAP immobilized on polystyrene microtiter wells.

After completing the remaining steps in the EIA (as described in Example 1), the absorbance at 405 nm was read. The results are shown in FIG. 3.

As shown, NHP dilutions of 1:32, 1:64, and 1:120 allowed SAP/G-2 binding to AAg. At higher NHP concentrations (e.g., dilution of 1:4, 1:8, 1:16), SAP/G-2 binding to AAg was inhibited, or interfered with, by other plasma components.

What is claimed is:

1. A method of binding aggregated immunoglobulin or immune complexes comprising contacting the aggregated immunoglobulin or immune complexes with serum amyloid P component (SAP) so that the SAP binds the aggregated immunoglobulin or immune complexes, the SAP being characterized in that it preferentially binds aggregated immunoglobulin or immune complexes in the presence of monomeric immunoglobulin.

2. The method of claim 1 wherein SAP is immobilized on a solid surface.

3. A method of detecting or quantitating immune complexes comprising:
   contacting the immune complexes with serum amyloid P component (SAP) immobilized on a solid surface so that the immune complexes bind to the SAP, the SAP being characterized in that it preferentially binds immune complexes in the presence of monomeric immunoglobulin; and
   detecting or quantitating the immune complexes bound to the SAP.

4. The method of claim 3 wherein the SAP is labeled to allow for the detection or quantitation of the immune complexes.

5. The method of claim 3 wherein a labeled component that binds to the immune complexes or to the SAP is added to allow the immune complexes to be detected or quantitated.

6. A test kit for detecting or quantitating immune complexes comprising a container holding SAP, the SAP being characterized in that it preferentially binds immune complexes in the presence of monomeric immunoglobulin.

7. The kit of claim 6 wherein the SAP is immobilized on a solid surface.

8. The kit of claim 6 wherein the SAP is labeled to allow for the detection or quantitation of the immune complexes.

9. The kit of claim 6 further comprising a container holding a labeled component that binds to the immune complexes or to the SAP to allow the immune complexes to be detected or quantitated.

* * * * *

UNITED STATES PATENT AND TRADEMARK OFFICE
CERTIFICATE OF CORRECTION

PATENT NO. : 5,221,628
DATED : June 22, 1993
INVENTOR(S) : Byron E. Anderson, et. al.

It is certified that error appears in the above-indentified patent and that said Letters Patent is hereby corrected as shown below:

Title page, col. 1, line 10, under the heading "OTHER PUBLICATIONS", delete "77:216a" and substitute therefor --77:2169--.

Column 2, line 62, delete "2:235-240" and substitute therefor --3:235-240--.

Column 3, line 24, after "characteristics" insert --Id.--.

Column 7, line 13, delete "suc" and substitute therefor --such--.

Column 11, line 50, delete "our" and substitute therefor --hour--.

Signed and Sealed this

Twentieth Day of September, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,221,628
DATED : June 22, 1993
INVENTOR(S) : Byron E. ANDERSON Et Al.

It is certified that error appears in the above-indentified patent and that said Letters Patent is hereby corrected as shown below:

ON THE TITLE PAGE

On the title page, column 1, line 8, after "Northwestern" please delete "Univeristy" and substitute therefor --University--.

Signed and Sealed this

Eighteenth Day of October, 1994

Attest:

BRUCE LEHMAN

*Attesting Officer*  *Commissioner of Patents and Trademarks*